United States Patent [19]

Hussein et al.

[11] Patent Number: 4,983,394

[45] Date of Patent: Jan. 8, 1991

[54] FLAVOR ENHANCING AND MEDICINAL TASTE MASKING AGENT

[75] Inventors: Mamoun M. Hussein, Mt. Lakes; Shirley A. Barcelon, Randolph, both of N.J.

[73] Assignee: Warner-Lambert Company, Morris Plains, N.J.

[21] Appl. No.: 518,369

[22] Filed: May 3, 1990

[51] Int. Cl.$^5$ .......................... A61K 9/20; A61K 9/26
[52] U.S. Cl. ........................................ 424/440; 424/49; 424/195.1; 424/439; 424/441; 424/465; 514/974
[58] Field of Search ................ 424/440, 441, 465, 49, 424/53, 195.1, 58; 514/974, 948

[56] References Cited

U.S. PATENT DOCUMENTS

| | | | |
|---|---|---|---|
| 4,064,184 | 12/1977 | Light | 260/617 R |
| 4,246,287 | 1/1981 | Mussinan et al. | 426/3 |
| 4,252,828 | 2/1981 | Mussinan et al. | 426/3 |
| 4,269,862 | 5/1981 | Sprecker et al. | 426/536 |
| 4,289,705 | 9/1981 | Sprecker et al. | 260/345.1 |
| 4,303,725 | 12/1981 | Sprecker et al. | 428/291 |
| 4,320,771 | 3/1982 | Sprecker et al. | 131/276 |
| 4,357,315 | 11/1982 | Boden | 424/49 |
| 4,431,680 | 2/1984 | Yoshida | 426/538 |

*Primary Examiner*—Thurman K. Page
*Assistant Examiner*—D. Gabrielle Phelan
*Attorney, Agent, or Firm*—Daniel A. Scola, Jr.

[57] ABSTRACT

Confections containing a volatile oil and designed for dissolving in the oral cavity containing novel volatile oil masking agents are disclosed. The volatile oil masking agents significantly suppress the perception of unpleasant organoleptic sensations such as bitterness or medicinal off-taste initiated by the volatile oil being released in the oral cavity. Masking agents such as fenchone and d-borneol are present in the confection in sensorially undetectable amounts to provide masking of unpleasant characteristics of volatile oils without detracting from the desired organoleptic sensations of taste and the preception of vapor action in the oral cavity.

10 Claims, No Drawings

FLAVOR ENHANCING AND MEDICINAL TASTE MASKING AGENT

BACKGROUND OF THE INVENTION

The present invention relates to improved confections which are intended to reside in the oral cavity for a period of time while being consumed. In particular, the present invention provides, among other things, medicinal tablets in which the medicinal off-taste commonly associated therewith is masked as the confection dissolves in the oral cavity.

Confections, and especially medicinal tablets which deliver active ingredients in the oral cavity, may be divided into various classes based upon their compositions or intended effect. Lozenges, compressed tablets and other medicinal tablets include breath fresheners, breath deodorants, cough suppressants, nasal decongestants and the like.

Over the years, considerable effort has been directed to improving sensory perception in the oral cavity of the volatile oils contained in confections. Often, such confections are perceived as having an unpleasant "medicinal" taste which tends to detract from the acceptance of such products. This unpleasant taste sensation is largely attributed to volatile oils included as part of the confection. Volatile oils or essential oils are derived from the leaves, stems or flowers of numerous plants and usually carry the savory or odorous principles of the plant obtained by distillation, expression or extraction. Volatile oils are known for their variable odors and distinctive tastes. Some are sweet, while others can be mild, pungent, hot, acrid, caustic or burning in taste. In addition, some volatile oils can be made synthetically. Masking the impression of volatile oil's medicinal off-taste in the oral cavity increases the benefit of the confection by ameliorating perceived bitterness, pungency, or other undesirable organoleptic sensations.

Menthol is isolated principally from the oil of *Mentha arvensis*. In its commercial form, menthol is present as 1-menthol crystals obtained from a process involving cooling of the oil. Fractional distillation of peppermint oil which usually contains from about 50% to about 65% menthol provides another important source of menthol. Synthetic sources of 1-menthol are also available.

The use of menthol for its medicinal effects is known in the art. Menthol's cooling effect to the mouth is useful to relieve local irritations in the throat and mouth.

Eucalyptus oil is another volatile oil thought to have therapeutic properties and is derived from the eucalyptus tree. Having a camphoraceous odor and cooling taste, this volatile oil is often combined with other essential oils such as those of menthol in confection formulations to impart medicinal effect. In particular, eucalyptus and its most active constituent, eucalyptol, are believed to be effective decongestants. Combinations of menthol and eucalyptus are widely used. When they are included in formulations capable of dissolving in the oral cavity, relief can be provided for coughs and minor mouth, throat, and upper respiratory irritations. Other uses of the methol/eucalyptus combination include mouthwashes, dentifrices and rubbing liniments.

Confections which include such medicinal formulations, e.g., cough drops, lozenges, etc., however, suffer from several shortcomings. For example, a bitter or "medicinal" taste and/or odor is often perceived due to the high potency of eucalyptus oil and eucalyptol. The strong taste and odor of the eucalyptus oil based confections released in the oral cavity, for example, provide an unpleasant organoleptic experience to many users, thus reducing the likelihood of continued treatment with the lozenge or tablet. In addition, prior art preparations containing eucalyptus suffer from erratic release of the eucalyptus vapors contained within the confection. Consequently, the cooling effect of eucalyptus has often been attenuated. These problems, therefore, tend to detract from the acceptance of eucalyptus-containing products as adjuncts in cough and cold therapy.

In addition to the above mentioned medicinal confections, oral hygiene products such as mouthwash may also contain menthol and/or eucalyptus as flavorants. While not ingested, these products also have been known to produce residual bitterness or medicinal off-taste in the oral cavity after expectoration of the oral hygiene product.

While not considered essential oils, borneol and fenchone are useful adjuvants in flavorings and, more importantly, in the fragrance industry. Borneol occurs in nature either as one of its enantiomers (levo or dextrorotatory) or as the racemic mixture. It can also be prepared synthetically. It has a camphor-like odor also described as a woody-peppery odor. In addition, borneol is characterized as having a burning taste. Borneol is most often found in incense-type of fragrances and room fresheners or pine odor products, however, to a lesser extent, borneol has been reported to be used in nut and spice flavors in trace amounts. Borneol is derived from natural sources such as trees found in Borneo. D-borneol occurs, for example, in camphor, rosemary, lavender and in olibanum oils, while 1-borneol occurs in oils or the pinaceae species. It, also, may be synthesized from camphor by hydrogen reduction or from alpha-pinene. The exo-isomer of borneol, iso-borneol, is not found in nature but is produce synthetically. This isomer has a similar organoleptic characteristic to borneol.

Fenchone is a ketone derived from oil of fennel and oil of thuja as well as from synthetic sources. Like borneol, fenchone has a camphoraceous odor and burning or bitter taste. Fenchone is most often used in industrial fragrances to mask odors. As a flavor chemical, fenchone is used in berry flavor and spice complexes or in certain type of liquor flavorings.

In the past, flavor and aroma enhancing or augmenting of volatile oil containing products has been undertaken. U.S. Pat. Nos. 4,269,862, 4,289,705, 4,303,725, and 4,320,771 all to Sprecker, et al. disclose enhancement of camphoraceous eucalyptus oil-like taste and/or fragrance in various products including foodstuffs with oxabicyclooctanes. This augmenting or enhancing, however, fails to solve the problem of medicinal off-tastes often associated with eucalyptus based products.

U.S. Pat. No. 4,252,828 to Mussinan, et al. discloses the use of synthetic bornyl ethyl ether to enhance or augment the flavor and/or aroma of various foodstuffs by imparting a camphoraceous, woody, eucalyptol-like aroma and taste to various flavoring adjuvants including essential oils.

U.S. Pat. No. 4,246,287 also to Mussinan, et al. discloses the use of fenchyl ethyl ether in a manner similar to that of bornyl ethyl ether to augment or enhance the flavor and/or aroma of various foodstuffs.

While the above mentioned patents to Mussinan, et al. disclose processes and compositions for augmenting or enhancing the flavor and/or aroma of foodstuffs with ethyl ethers of bornyl and fenchyl, there was no teaching or suggestion as to alcohol or ketone moieties such as d-borneol and fenchone having the ability to be combined with eucalyptus-containing confections to reduce or suppress the medicinal off-taste and commonly associated bitterness.

It is, therefore, an object of the present invention to provide an improved confection having the bitterness or medicinal off-taste of essential oils combined therein suppressed upon release of the essential oil into the oral cavity.

Another object of the present invention is to provide a natural food additive which masks the bitterness and unpleasant organoleptic sensations of essential oils as they are released in the oral cavity.

SUMMARY OF THE INVENTION

In accordance with the present invention, there is provided an improved confection composition containing a volatile oil which suppresses the impact of the medicinal off-taste and odor associated with known volatile oils upon the confection dissolving in the oral cavity. The flavor impact and vapor action of confections are enhanced by providing a volatile oil masking agent in the confection which masks perceived undesirable organoleptic sensations such as medicinal-like bitter off-taste and/or odor when the volatile oil is released. The masking agent is present in an amount which is sensorially undetected in the oral cavity so that the desired aroma and flavor of the volatile oil is perceived without separate detection by the user of the masking agent.

In a preferred embodiment, the volatile oil masking agent is selected from borneol and fenchone. The masking agent may be present in an amount of from about 0.3 to about 50 parts per million (ppm) of the confection by weight. In a preferred embodiment, the masking agent is present in an amount of from about 5 to about 40 ppm while in a most preferred embodiment, from about 10 to about 30.

The flavor imparting and vapor action properties of the confection may be provided by volatile oils selected from both natural and synthetic sources. Typically, the volatile oil is present in an amount of from about 0.05% to about 1.0% by weight of the confection. The amount and type of volatile oil varies, however, in accordance with the desired flavor and whether or not vapor action is sought. In addition, the confection may contain a blend of volatile oils and other sweeteners to provide the desired flavor in the oral cavity. Examples of suitable volatile oils include spearmint, eucalyptus, peppermint, menthol and wintergreen (methyl- salicyclate) oils. Additionally, the confections of the present invention may also include sweeteners such as sugar, sugar alcohols, and sugar substitutes as part of the confection base.

In one embodiment, there is provided a confection containing a blend of eucalyptus and l-menthol and the medicinal off-taste masking agent to ameliorate the perceived bitterness of the volatile oil combination and improve vapor action. The above-mentioned combination is useful in cough and cold therapy as well as having a decongestant effect in the nasal cavity.

Also provided is a method of enhancing sensory perception of a volatile oil in the oral cavity. The volatile oil is contained within a confection designed to dissolve in the oral cavity. The confection also contains an amount of a volatile oil off-taste masking agent which is sensorially undetected in the oral cavity to modify the organoleptic perception of the volatile oil released by the dissolving confection. Undesirable organoleptic sensations such as bitterness are muted, yet the masking agent is undetected as a separate agent.

Unlike prior art approaches to flavor modification of volatile oil containing comestibles, the present invention's use of off-taste masking agents to enhance the flavor delivery of volatile oils is achieved without the sensorial perception of the volatile oil's undesirable flavor characteristics. Indeed, the masking qualities of borneol and fenchone on essential oils has heretofore been unrealized. The prior art also does not disclose or suggest the ability of the above agents to enhance the vapor action of essential oils as they are released from confections into the oral cavity.

As a result of the present invention, improved confectionery products are provided which have substantial reductions in unpleasant organoleptic sensations such as bitterness or medicinal taste upon the release of the volatile oil from the confection in the oral cavity. Further, in confections where eucalyptus oil is present, the masking agent provides in the oral cavity for improved vapor action of eucalyptus.

For a better understanding of the present invention, together with other and further objects, reference is made to the following description and its scope will be pointed out in the appended claims.

DETAILED DESCRIPTION OF THE INVENTION

It has now been surprisingly found that the disadvantages associated with confections containing a volatile oil which imparts a bitter taste upon release in the oral cavity can be overcome by using the novel method and composition of the present invention. The novel confection contains a volatile oil and a masking agent present in an amount which is undetected in the oral cavity but nevertheless has the ability to suppress sensory perception of volatile oil off-taste in the oral cavity.

In a preferred embodiment, the confection contains both menthol and eucalyptus as the volatile oil component and the volatile oil masking agent is selected from d-borneol and fenchone present in an amount of from about 0.3 to about 50 ppm. In this embodiment, the confection confers medicinal benefits by providing active ingredients which relieve irritations of the nasopharyngeal region caused by coughing as well as providing a vapor action decongestant effect.

In an alternative embodiment, there is also provided a confection which contains non-medicinal volatile oils which impart a flavor sensation upon dissolving in the oral cavity. In this embodiment, the confection also contains a volatile oil masking agent which enhances the impact of the volatile oil released from the confection while suppressing undesired taste sensations in the oral cavity. The volatile oil suppressing agent is also capable of being included in the oral hygiene products having volatile oil flavorings such as mouthwashes and dentifrices to suppress perceived bitterness, pungency, or other undesirable organoleptic sensation.

The preparation of confectionery formulations is historically well known and has changed little through the years. Confectionery items have been classified as either "hard" confectionery or "soft" confectionery. The volatile oil-modifying agent of the present invention can be incorporated by admixing the modifying agent into conventional hard and soft confections.

Hard confectionery may be processed and formulated by conventional means. In general, a hard confectionery has a base composed of a mixture of sugar and other carbohydrate bulking agents kept in an amorphous or glassy condition. This form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavorings, sweeteners, acidulants, colorants and so forth may also be added.

Such confectionery may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° to 170° C. in a few minutes. The candy is then rapidly cooled to 100° to 120° C. and worked as a plastic-like mass enabling incorporation of the additives, such as flavors, colorants and the like.

In vacuum cookers, the carbohydrate bulking agent is boiled to 125° to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavors, colorants and other additives during conventional manufacturing of hard confectionery is determined by the time needed to obtain a uniform distribution of the materials. Normally, mixing times of from 4 to 10 minutes have been found to be acceptable.

Once the candy mass has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets*, Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and selection of the specific apparatus will be apparent to the artisan.

Similar to hard confectionery, soft confectionery may be utilized in this invention. The preparation of soft confections, such as nougat, involves conventional methods, such as the combination of two primary components, namely (1) a high boiling syrup such as corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. A general discussion of the composition and preparation of nougat confections may be found in B.W. Minifie, *Chocolate, Cocoa and Confectionery: Science and Technology*, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor may be added. The mixture is further mixed for an additional period until it is ready to be removed and formed into suitable confectionery shapes.

The flavoring components of the confection are flavors having an associated bitter taste or other unpleasant after taste. These flavoring components may be chosen from natural and synthetic flavoring liquids such as volatile oils, synthetic flavor oils, flavoring aromatic and oils, liquids, oleoresins or extracts derived from plants, leaves, flowers, fruits, stems and combinations thereof. Non-limiting representative examples of volatile oils include spearmint oil, cinnamon oil, oil of wintergreen (methyl salicylate), peppermint oil, menthol, clove oil, bay oil, anise oil, eucalyptus oil, thyme oil, cedar leaf oil, oil of nutmeg, allspice oil, oil of sage, mace extract, oil of bitter almond, and cassia oil. In addition, the confection may also contain artificial, natural or synthetic flavors including fruit flavors such as vanilla, and citrus oils including lemon, orange, grape, lime and grapefruit and fruit essences including apple, pear, peach, grape, strawberry, raspberry, cherry, plum, pineapple, apricot and so forth.

Other useful flavorings include aldehydes and esters such as benzaldehyde (cherry, almond), citral, i.e., alphocitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof and the like.

In the instance where sweeteners are utilized, the present invention contemplates the inclusion of those sweeteners well known in the art, including both natural and artificial sweeteners. The sweeteners may be chosen from the following non-limiting list: sugars such as sucrose, glucose (corn syrup), dextrose, invert sugar, fructose, and mixtures thereof, saccharin and its various salts such as the sodium or calcium salt; cyclamic acid and its various salts such as the sodium salt; the dipeptide sweeteners such as aspartame, dihydrochalcone compounds, glycyrrhizin; Stevia Rebaudiana (Stevioside); chloro derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated as an additional sweetener is the non-fermentable sugar substitute (hydrogenated starch hydrolysate) which is described in U.S. Pat. No. Re. 26,959. Also contemplated is the synthetic sweetener 3,6-dihydro -6-methyl1-1-1,2,3-oxathiazin-4-one-2,2-dioxide, particularly the potassium (acesulfam-K), sodium and calcium salts thereof as described in German Pat. No. 2,001,017.7. Also contemplated as bulking agents are polydextrose, PALATINIT®, and modified starches, e.g. maltodextrins.

In addition, the confection may also contain suitable auxiliary flavorings including both natural and artificial flavors, and mints such as peppermint, artificial vanilla, cinnamon, various fruit flavors, both individual and mixed. Such flavorings are generally utilized in amounts that will vary depending upon the particular confection and volatile oil selected.

The confection may also include a colorant. The colorants may be selected from any of the numerous dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino) diphenylmethylane]-[1-(N-ethyl-N-p-sulfoniumbenzyl)2-5-cyclohexadieneimine]. A full recitation of all FD&C and D&C dyes and their corresponding chemical structures may be found in the *Kirk-Othmer Encyclopedia of Chemical Technology*, in Volume 5, pages 857–884, which is incorporated herein by reference.

The volatile oil off-taste masking agent is preferably selected from d-borneol or fenchone. To effect the novel off-taste suppressing properties of the present invention, the masking agent is present in an amount of from about 0.3 to about 50 ppm of the confection. The preferred range of masking agent is from about 5 to about 40 ppm while the most preferred range is from about 10 to about 30 ppm of the confection.

The suppressing agent borneol is an alcohol and is commercially available as a pure crystalline material. Fenchone, on the other hand, is a ketone and is available as a pure liquid which solidifies at 6° C.

Although borneol and fenchone are considered to be potent sources of camphoraceous odor, it has now been found that the above compounds also effectively mask unpleasant medicinal off-tastes often associated with confections containing volatile oils, and especially eucalyptus. Key, however, to the present invention is the discovery that when the masking agents are present in confections in amounts ranging from about 0.3 ppm to about 50 ppm, the masking agents are undetectable in the oral cavity and in addition provide vapor action well in excess of the vapor action expected from the mere addition of the two vaporous components, especially with eucalyptus.

With respect to confectionery compressed tablet formulations, such will contain a tablet granulation base and various additives such as sweeteners and flavors. The tablet granulation base employed will vary depending upon various factors such as the type of base used, friability desired and other components used to make the final product. The confectionery compressed tablet made in accordance with the present invention however contains a volatile oil and a volatile oil-masking agent in amounts similar to the above cough drop example. These confections generally contain sugars in amounts up to 95% by weight of the composition. The confectionery compressed tablet may additionally include the conventional tablet excipients such as binders and lubricants as well as flavoring agents, coloring agents.

It is also contemplated that oral hygiene products such as dentifrices and mouthwashes flavored with volatile oils will likewise benefit from the medicinal off-taste masking agents of the present invention. The addition of borneol and/or fenchone in amounts ranging from about 0.3 to about 50 ppm of the product provide significant amelioration of the objectionable bitter off-taste often associated with the residual flavor sensation after the product has been expectorated.

The variations that one may practice with regard to the above-mentioned confections and oral hygiene products are wide ranging and within the ability of those skilled in the art particularly with regard to the use of additional composition fillers, flavoring adjuncts, the use of coloring agents, etc.

As previously mentioned, the volatile oil component of the confection may include menthol. In particular, the most important commercial product is 1-menthol. Commercial 1-menthol is isolated principally from the oil of *Mentha arvensis*. It is also produced by synthesis. The process involves cooling of the oil and purifying the crystals formed. Menthol possess a distinct peppermint flavor and gives the impression of cooling the mouth and skin.

L-menthol and eucalyptus oil may be combined to provide the volatile oil component of the confection. When so combined, the menthol-eucalyptus is useful as an adjunct to cough and cold therapy. Eucalyptus is believed to impart decongestant type activity while menthol provides soothing of the mouth and throat areas. When a volatile oil-masking agent is combined with the above volatile oil combination menthol-eucalyptus, it has been found that the masking agent substantially suppresses the unpleasant organoleptic experience often detected when confectionery formulations containing the above ingredients dissolve in the oral cavity. In addition, the vapor action of eucalyptus is enhanced by including the masking agents of the present invention.

The masking agents of the present invention may also be combined with other volatile oil enhancing agents to provide additional benefits in confections designed to reside in the oral cavity. For example, borneol, isoborneol and/or fenchone may be added to confection formulas containing volatile oil modifying agents, capsicum and capsicum oleoresin, as disclosed in commonly assigned and co-pending U.S. Patent Application Ser. No. 071,518,360 entitled "Flavor Enhancing And Increasing Efficacy Of Cough Drops", the disclosure of which is incorporated by reference herein.

Tests were conducted by using the confection of the present invention to compare it with confection products not containing a volatile oil-masking agent, and it was found that not only were the bitter off-taste masking properties of d-borneol and fenchone evident but also that additional or divergent tastes were undetectable in the inventive confections.

EXAMPLES

The following examples serve to provide further appreciation of the invention but are not meant in any way to restrict the effective scope of the invention.

EXAMPLE 1

A menthol and eucalyptus oil blend was prepared using the following formulation:

| INGREDIENT | PERCENT BY WEIGHT |
|---|---|
| Menthol | 52.53 |
| Eucalyptus oil | 47.47 |
| (80-85% BBA) | 100.00 |

The above volatile oil blend was thereafter included in candy confections prepared in accordance with the present invention and a control for comparative testing and sensory evaluation. Sample A contained the masking agent d-fenchone and Sample B contained borneol. The formulae of the respective compositions are set forth in Table 1 below. All formulae are expressed on a weight-weight basis.

TABLE 1

| INGREDIENT | CONTROL | SAMPLE A | SAMPLE B |
|---|---|---|---|
| Candy Base | 99.64 | 99.635 | 99.635 |
| Menthol/Eucalyptus blend | 0.36 | 0.360 | 0.360 |
| d-Fenchone | — | 0.005 | — |
| Borneol | — | — | 0.005 |
|  | 100.00 | 100.000 | 100.000 |

The confections made according to the above formulae were evaluated by an experienced taste panel to determine the masking abilities of d-fenchone and borneol. The results are set forth below.

|  | EXPERT PANEL TESTING | | |
|---|---|---|---|
| SPECIMEN | OFF-TASTE MASKING | BITTERNESS | FLAVOR |
| Control | 0 | +++ | Good |
| A | ++ | + | Excellent |
| B | ++ | + | Excellent |

Inventive Samples A and B were judged to be more pleasing overall than the Control. Bitterness was found to be significantly reduced along with substantial masking of the commonly perceived medicinal off-taste as compared with the Control. In addition, the cooling effect of menthol was more pronounced in the inventive sample containing fenchone.

EXAMPLE 2

In this Example, the inventive off-taste masking properties of the compounds of the present invention are compared at levels lower than that of Example 1 in sugar fondants. The fondants were prepared in a manner similar to Example 1 in that a Control formulation and two invention formulations were prepared and a menthol-eucalyptus blend was selected as the volatile oil. Sample C contained the masking agent fenchone whereas Sample D contained d-borneol. The Samples were prepared according to the following formulae as set forth in Table 2. All formulae are expressed on a weight-weight basis.

TABLE 2

| INGREDIENT | CONTROL | C | D |
|---|---|---|---|
| Sugar Fondant (12% water) | 99.70 | 99.70 | 9.70 |
| Menthol/Eucalyptus blend | 0.20 | 0.20 | 0.20 |
| d-Fenchone | — | 0.001 | — |
| Borneol | — | — | 0.001 |
| NOTE - doesn't add up to 100% | 99.90 | 99.91 | 99.91 |

The fondants were thereafter evaluated by an experienced taste panel to determine the masking properties of the compounds d-fenchone and borneol at these lower levels. The results are set forth below.

|  | EXPERT PANEL TESTING | | |
|---|---|---|---|
| SPECIMEN | OFF-TASTE MASKING | BITTERNESS | FLAVOR |
| Control | 0 | +++ | Good |
| C | ++ | + | Excellent |
| D | ++ | + | Excellent |

Referring now to the Panel testing results, it can be seen the fondants prepared in accordance with the present invention to include a volatile oil-masking agent provided favorable results when compared to the Control sample. Even at levels of 10 ppm, significant masking of the harshness and/or bitterness associated with eucalyptus containing confections was achieved with both d-fenchone and borneol. When compared to the fondant control, inventive Samples C and D were reported to have significant reductions in medicinal off-taste as reported in the terms of harshness and bitterness. In addition, the eucalyptus taste was reported to be milder, as a result of including either d-fenchone and/or borneol.

EXAMPLE 3

In this Example, the off-taste masking properties of the compounds of the present invention were included in hard boiled cough drop formulae for comparison purposes against a control cough drop without a masking agent. The Samples were prepared as follows:

| INGREDIENT | CONTROL | E | F |
|---|---|---|---|
| Sugar/Corn Syrup base | 99.44 | 99.4400 | 99.4400 |
| Citric Acid | 0.20 | 0.2000 | 0.2000 |
| Menthol/Eucalyptus blend | 0.36 | 0.3575 | 0.3575 |
| d-Fenchone | — | 0.0025 | — |
| Borneol | — | — | 0.0025 |

The cough drops were then subjected to taste Panel testing in a manner similar to Examples 1 and 2. The results are set forth below.

|  | EXPERT PANEL TESTING | | |
|---|---|---|---|
| SPECIMEN | MASKING | BITTERNESS | FLAVOR |
| Control | 0 | +++ | Good |
| E | +++ | + | Excellent |

| | EXPERT PANEL TESTING | | |
|---|---|---|---|
| SPECIMEN | MASKING | BITTERNESS | FLAVOR |
| F | ++ | + | Excellent |

In similar results to those obtained in Examples 1 and 2, Inventive Samples E and F were again found to be more pleasing overall than the Control. Bitterness, as well as medicinal off-taste, were judged to be significantly reduced with both inventive samples as compared to control.

As can be seen from the foregoing Examples, the volatile oil masking agents of the present invention provided favorable results when compared to control samples. In the past, confections containing volatile oil and designed to reside in the oral cavity for a period of time often provided undesirable bitterness and a medicinal off-taste. The inventive confections, on the other hand, clearly demonstrate significant reductions in the above-mentioned distractive organoleptic sensations by including volatile oil masking agents.

Thus, while there has been described what are presently believed to be the preferred embodiment of the present invention, and further embodiments will be realized by those skilled in the art, and it is intended to claim all such embodiments as come within the true scope of the invention.

What is claimed is:

1. A confection for dissolving in the oral cavity comprising:
    (a) ingestible volatile flavor oil; and
    (b) volatile oil mellowing, suppressing and bitterness-reducing agent selected from the group consisting of fenchone, borneol and iso-borneol in an amount which is sensorially undetected in the oral cavity but sufficient to modify sensory perception of said volatile oil as it is released in the oral cavity said amount being about 0.3 to 50 parts per million (ppm) by weight of said confection.

2. The confection of claim 1 wherein said agent is present in an amount of from about 2 to about 40 parts per million (ppm) by weight of said confection.

3. The confection of claim 1 wherein said agent is present in an amount of from about 10 to about 25 parts per million (ppm) by weight of said confection.

4. A mouthwash comprising:
    (a) an ingestible volatile flavor oil; and
    (b) a volatile oil mellowing agent selected from the group consisting of fenchone and d-borneol in an amount which is sensorially undetected in the oral cavity said amount being about 1 to about 75 ppm but sufficient to modify sensory perception of said volatile oil while it is present in the oral cavity.

5. The mouthwash of claim 4 wherein said volatile oil is eucalyptus.

6. The mouthwash of claim 4 wherein said mellowing agent is present in an amount of from about 5 to about 40 ppm.

7. Method of mellowing and reducing bitterness and off-taste of ingestible volatile flavor oil-containing comestibles comprising:
    providing a volatile oil mellowing, suppressing, and bitterness-reducing agent selected from the group consisting of borneol, fenchone and mixtures thereof in an amount which is sensorially undetected in the oral cavity but sufficient to mellow, reduce the bitterness and off-taste of said volatile oil as it is released in the oral cavity said amount being from about 0.3 to about 50 ppm by weight of said comestible.

8. The method of claim 7 wherein said volatile oil is selected from the group consisting of menthol, 1-menthol, anise, caraway, cinnamon, clove, coriander, eucalyptus, fennel, lavender, lemon, orange, orange flower, peppermint, pine needle, spearmint, and mixtures thereof.

9. The method of claim 7 wherein said agent is present in an amount of from about 2 to about 40 ppm by weight of said comestible.

10. The method of claim 7 wherein said agent is present in an amount of from about 10 to about 25 ppm by weight of said comestible.

* * * * *